United States Patent [19]

Pisoni

[11] Patent Number: 5,445,801
[45] Date of Patent: Aug. 29, 1995

[54] MULTITUBE FALLING-FILM REACTOR

[75] Inventor: Carlo Pisoni, Busto Arsizio, Italy

[73] Assignee: Meccaniche Moderne S.r.l. Chemical Plants Division, Busto Arsizio, Italy

[21] Appl. No.: 63,250

[22] Filed: May 18, 1993

[30] Foreign Application Priority Data

May 19, 1992 [IT] Italy ................ MI92A1198

[51] Int. Cl.$^6$ ............................... B01J 10/02
[52] U.S. Cl. .................. 422/197; 261/112.1; 422/129; 562/123
[58] Field of Search ............ 422/129, 198, 200, 201, 422/188, 196–197; 261/108, 112.1, 153, 160; 562/123

[56] References Cited

U.S. PATENT DOCUMENTS

| | | | |
|---|---|---|---|
| 3,531,518 | 9/1970 | Ohren et al. | 562/123 |
| 3,535,339 | 10/1970 | Beyer et al. | 562/123 |
| 3,667,919 | 6/1972 | Denzler et al. | 422/310 |
| 3,918,917 | 11/1975 | Ashina et al. | 261/112.1 |
| 4,036,596 | 7/1977 | Ogoshi et al. | 261/112.1 |
| 4,059,621 | 11/1977 | Johnson, Jr. | 562/123 |
| 4,183,897 | 1/1980 | Lanteri | 261/112.1 |

FOREIGN PATENT DOCUMENTS 2449665  9/1980 France.

*Primary Examiner*—Robert J. Warden
*Assistant Examiner*—L. M. Crawford
*Attorney, Agent, or Firm*—Bucknam and Archer

[57] ABSTRACT

Mulitube falling-film reactor for the continuous sulfonation and sulfation of fluid-state organic substances by reaction with gaseous sulphuric anhydride (SO$_3$), has each tubular element non-permanently fixed to the plates and has a nozzle (10) fitted in a sleeve (20) integral with a reaction tube (23). The nozzle (10) can slide within the sleeve (20) and may be placed at different heights with respect to the latter, forming with the end-piece (14) a cylindrical crown opening (18) of fixed width and variable height. Such arrangement permits to control the delivery of the fluid to be sulfonated. The opposite end of each tube (23) fits into a double-plate seal system.

5 Claims, 3 Drawing Sheets

MULTITUBE FALLING-FILM REACTOR

FIELD OF THE INVENTION

This invention refers to a multitube falling-film reactor, utilizable in particular for the continuous sulfonation and the sulfation of fluid-state organic substances by reaction with gaseous sulphuric anhydride ($SO_3$).

Reactors of this type are well known in the art and are available on the market. They are essentially constituted by a nest of tubes wherein the tubes are permanently fixed to at least one plate.

The organic substance and the $SO_3$, opportunely diluted with air at a concentration of about 4%, are fed from above within the tubes, while a cooling fluid, generally water, is provided externally to the tubes to absorb the heat of the reaction (exothermic). In order to obtain high yields and a sulfonated or sulfated product of good quality, reaction must take place uniformly in each tube of the reactor.

To obtain this result, the reagents should be distributed homogeneously and constantly in each tube of the reactor. However, while for $SO_3$ this uniform distribution takes place spontaneously, as this reagent is fed at a constant pressure in the gaseous phase, for the organic substance, on the contrary, a control system must be provided in the various tubes in order to obtain the necessary distribution uniformity. At present, various control systems are utilized, all of which have a distributor on top of each tube provided with a slit or orifice whose section can be mechanically adjustable in various ways.

These systems permit a poorly precise control of the delivery. Actually, minor variations in the passage sections suffice to produce rather high delivery variations, which prevent the organic substance from reaching an optimum distribution uniformity in all the tubes. Besides, the known reactors show another drawback which adds to the above mentioned inconvenience. In fact, they are produced with tubes that are permanently fixed to the plates and therefore they cannot be easily removed, should they break. As a consequence, maintenance operations are needed which are rather wearisome and lengthy, to have the reactor repaired.

Now, the applicant has devised the multitube falling-film reactor subject of this invention, utilizable in particular for sulfonation and sulfation reactions, which permits to eliminate all the above mentioned drawbacks of the known reactors of the known types.

SUMMARY OF THE INVENTION

An object of this invention is therefore a reactor comprising:

a) a very simple and precise control system of the delivery of the fluid-state organic composition to be sulfonated or sulfated, based on the formation, on top of each tube, of a cylindrical crown opening placed between a concentric nozzle and sleeve unit. The internal nozzle can slide within the external sleeve, integral with a reaction tube and may be placed at various heights. Such arrangement permits to have fixed width and variable height openings, which allow for variations in the charge loss in the splits, such as to produce flow variations, utilizable to control and make uniform the fluid flow in the various tubes of the reactor. The precision and accuracy of this control system ensue from the fact that even minor delivery variations—allowing for very exact and easily reproducible calibrations—can be obtained through rather high and easily controllable vertical shifts of the nozzle;

b) nest of tubes non permanently fixed to the plates, but blocked to the latter by means of systems with flanges, ring nuts and seals. Such tubes can be easily taken out and may be replaced in a very short time;

c) adoption on the reactor outlet side (lower side) of a double plate seal system, which permits to avoid, in case of loss from the first plate, any infiltration of cooling water into the reaction fluid, which would cause its pollution and the onset of corrosion phenomena downstream of the reactor.

BRIEF DESCRIPTION OF THE DRAWINGS

The structures of such a reactor object of this invention shall clearly appear from the following detailed description, wherein reference is made to the attached drawings which represent a preferred embodiment, to be construed as a non-limitative example, and wherein.

Figure 1:
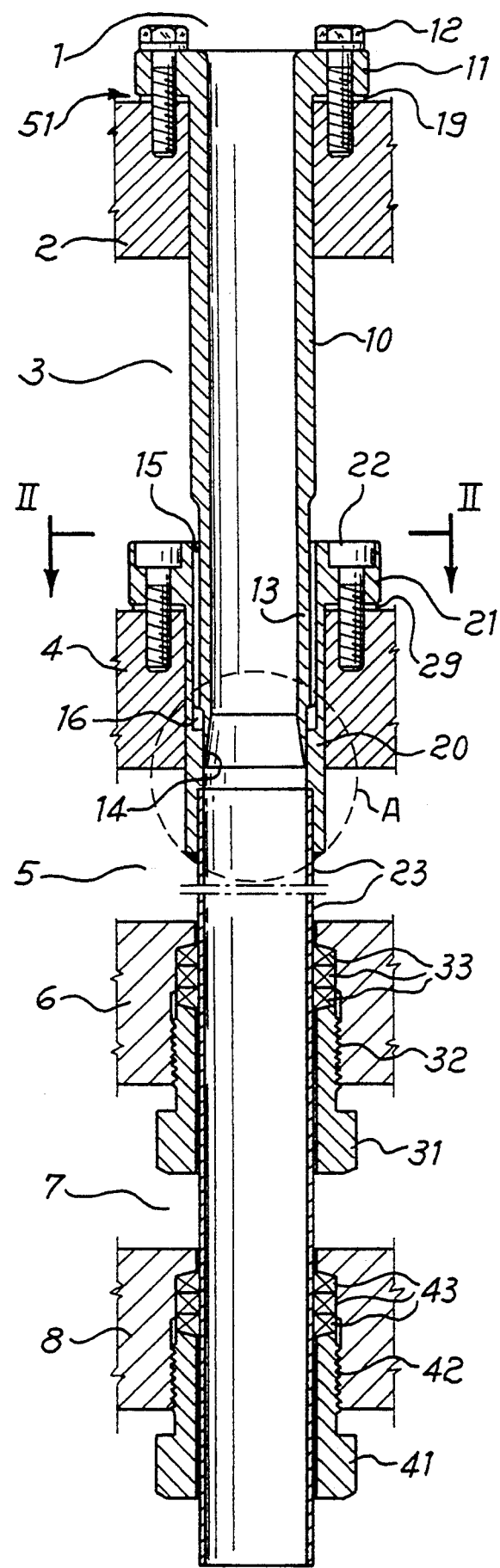
FIG. 1 is a longitudinal section of a tubular element of the multitube reactor object of this invention.
Figure 2:
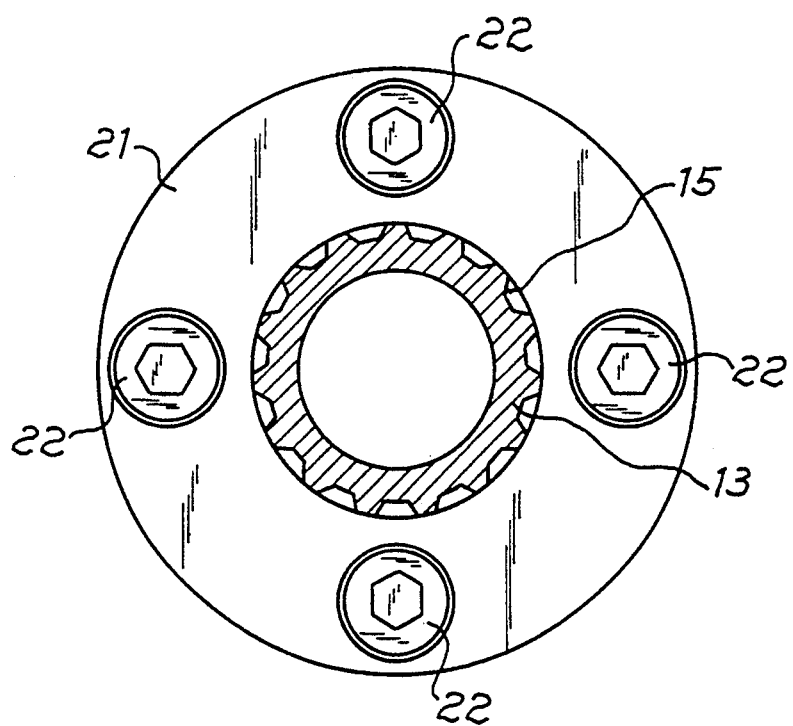
FIG. 2 is an enlargement of the II—II cross section of FIG. 1.
Figure 3:
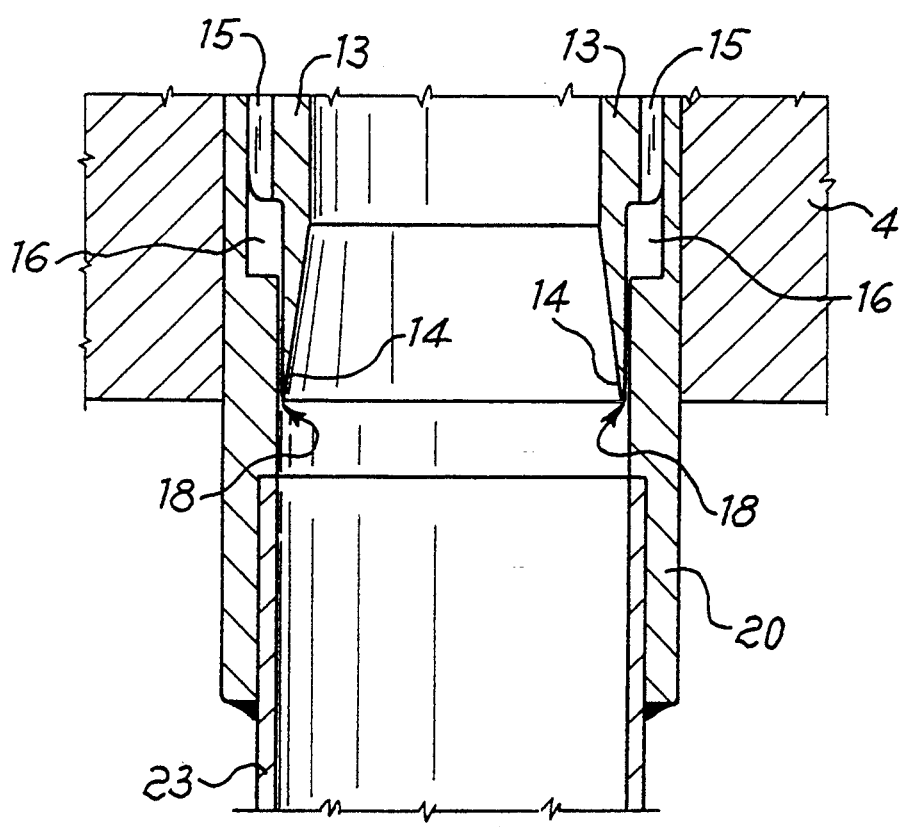
FIG. 3 is an enlargement of detail A of FIG. 1.
Figure 4:
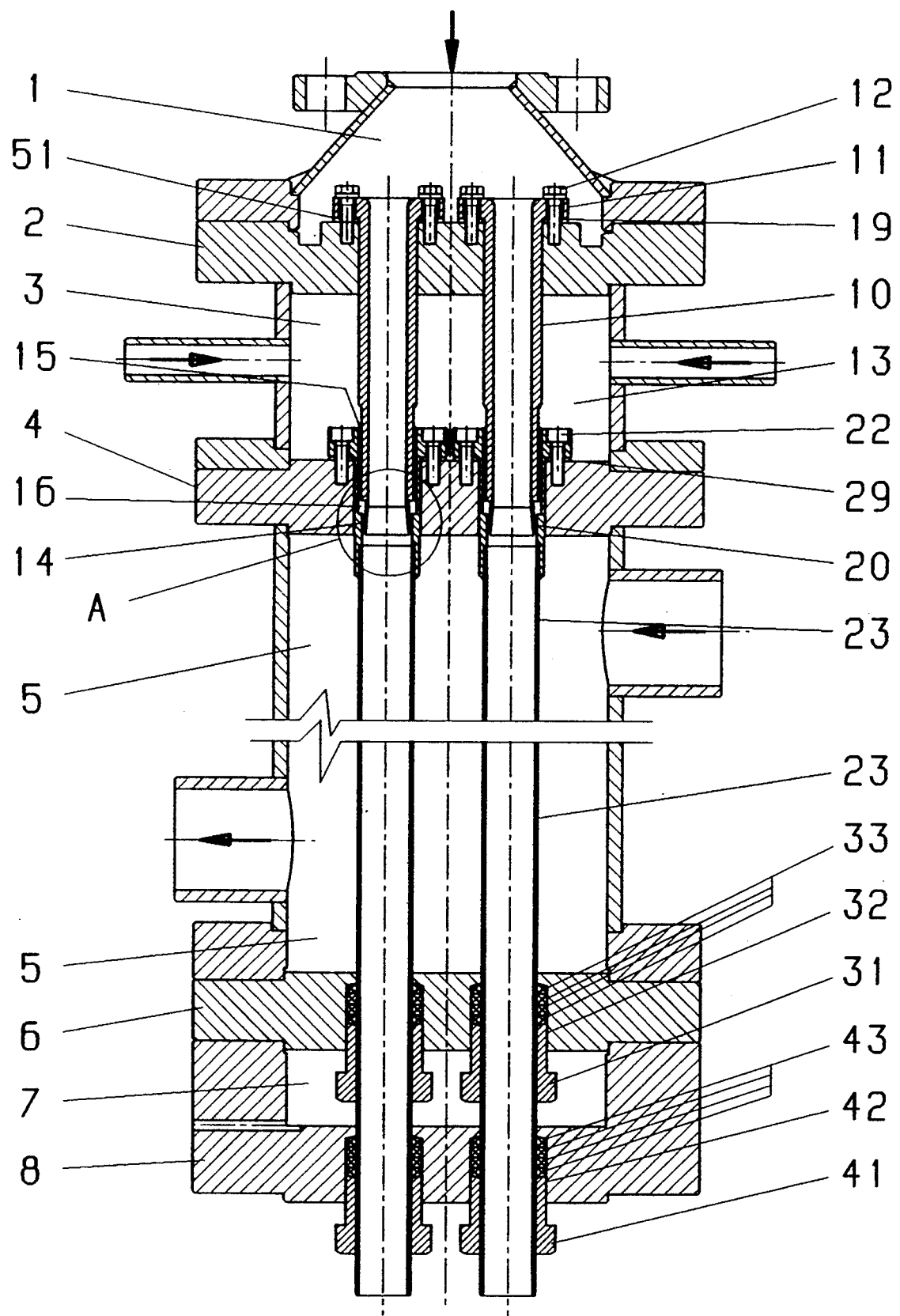
FIG. 4 is a longitudinal section of the reactor of this invention.

With reference to the above drawings, the reactor is represented, by way of example, by a single tubular element.

A top cap, bounds a chamber 1 of distribution of the gaseous $SO_3$ in the various tubes, placed upon a first top plate 2. Nozzles 10 fit in special holes of said plate, said nozzles having each an edge 11, utilized to fix the nozzle to said plate by means of screws 12 and gaskets 19. Each nozzle 10 comprises a lower part 13 having a toothed-wheel-shaped radial section and a lower end-piece 14.

Such lower part 13 fits into a sleeve 20, which, in its turn, fits into a special hole provided in a second top plate 4, to which it is fixed along edge 21 by means of screws 22 and gaskets 29. At both ends of said sleeve 20, projecting under plate 4, a reaction tube 23 is connected. This connection is made in such a way as to cause the internal wall of said tube 23 to be flush with the internal wall of said sleeve 20.

A chamber 3 of distribution of the fluid to be sulfonated or sulfated is placed between the first top plate 2 and the second top plate 4. From this chamber, the fluid flows in the longitudinal channels 15 provided in the lower part 13 of nozzle 10, collects in a cavity 16 and then flows down from a cylindrical crown-shaped opening 18 provided between the inner wall of the lower part of sleeve 20 and the external wall of end-piece 14 of nozzle 10, forming a film that flows down along the internal wall of tube 23 and that reacts with $SO_3$ which moves in concurrent.

The width of each circular crown of each opening 18 is fixed and calibrated in function of the fluid to be fed. Generally, it has a constant value in all tubes, comprised between 0.15 and 0.50 mm, and preferably between 0.25 and 0.35 mm. On the contrary, the height of each opening 18 can be changed by raising or lowering nozzle 10, so as to obtain charge losses through said opening, and, therefore, variations in the delivery of fluid fed to reaction tube 23. Such an arrangement permits to calibrate, with the utmost precision and accuracy, the fluid delivery into the various tubes of the reactor, making the distribution uniform in each tube and making up in this way for the flow differences which would create in the tubes, due to unavoidable, however minor, width differences in the various openings 18. In practice, such calibration operation is made by utilizing varying thickness strips 51, calibrated to thickness differences of 0.01-2.0 mm, which are fitted between the edge of each nozzle 10 and gasket 19, until a uniform fluid flow is obtained in all tubes.

The lower end of each tube 23 is fitted in a double plate system. In fact, the reactor comprises a first lower plate 6 and a second lower plate 8, both of them having non permanently fixed through-tubes. On each tube 23, the seal is provided respectively by braid-gaskets 33 and 43, which are set against tube 23 by ring nuts 31 and 41, when these latter are screwed, through threads 32 and 42 to said plates. Such double plate system prevents any possible infiltration of the pressurized cooling water in zone 5—provided on the outside of the tubes—from ending up in the reaction substance, giving rise in this way to the aforementioned problems.

This infiltration would cause the cooling water to collect in fact in the air gap at atmospheric pressure in zone 7 on the reactor outside, between the two plates 6 and 8.

The reactor according to the above described invention permits an easy and rapid taking out of any tube, if a change should be needed.

While the invention has been described with reference to a specific embodiment, many alternatives and changes may be obviously made by the experts in the light of the above description. Hence the invention embraces all the alternatives and changes which fall within the spirit and protection scope of the following claims.

I claim:

1. A multitube falling-film reactor for the continuous sulfonation and sulfation of a liquid organic substance by reaction with gaseous sulphuric anhydride $SO_3$, consisting essentially of a plurality of tubular elements means for feeding said liquid organic substance, each tubular element consisting essentially of a nozzle (10) fitted in a first top plate (2); said nozzle comprising a lower part (13), a sleeve (20) fitted in a second top plate (4), said lower part of said nozzle fitting into said sleeve; a reaction tube (23) fixed to said sleeve (20) and projecting under said second top plate (4); said sleeve having an internal surface and a lower part, said reaction tube having a lower end and an internal surface and being placed in such a way as to cause its internal surface to be flush with said internal surface of said sleeve (20), said lower end of said reaction tube fitting into a double plate system comprising plates (6) and (8), said means for feeding said liquid organic substance is provided with a first distribution chamber (3) placed between said first and second top plates (2) and (4) for feeding said liquid organic substance, said lower part of said nozzle is provided with longitudinal channels (15), defined by said lower part of said nozzle and said internal surface of said sleeve, said liquid organic substance flows through said longitudinal channels (15), collects in a cavity (16), said nozzle (10) has a lower end piece (14), said lower end piece having an external wall, a cylindrical crown-shaped opening (18) being provided between said inner wall of said lower part of said sleeve (20) and said external wall of said lower end piece (14), said opening (18) having constant width and a lower end, said liquid organic substance then flowing down from said cylindrical-crown-shaped opening (18), forming a fluid film which flows down along said internal walls of said reaction tube (23), where it reacts with said gaseous $SO_3$ which moves concurrently thereto, a second distribution chamber (1) being placed upon said first top plate (2) and under a top cap for introducing $SO_3$ at the level of said lower end of said opening (18), wherein said longitudinal channels (15) are defined by a toothed profile radial section of the lower part of said nozzle and said nozzle is adapted to slide within said sleeve (20) and may be placed at different heights.

2. The reactor according to claim 1 which is provided with steel strips (51) calibrated with thickness differences of 0.01-2 mm; said nozzle (10) has an edge, said steel strips are fitted between said edge and a gasket and wherein the height of said opening (18) is varied by raising or lowering said nozzle (10) by means of said steel strips (51), whereby variations in the flow of said liquid organic substance are obtained and the flow of said liquid organic substance becomes uniform in said plurality of tubular elements.

3. The reactor according to claim 2, wherein said nozzle has an edge (11), a gasket (19) and a screw (12) fixing said nozzle to said first top plate (2), said reactor is provided with steel strips (51) and calibrated with thickness differences of 0.01-2.0 mm, said strips being fitted between said edge (11) and said gasket (19), whereby variations in the flow of said liquid organic substance are obtained and the flow to all the tubes of said reactor is uniform.

4. The reactor according to claim 3, wherein said opening (18) has a width between 0.25 and 0.35 mm in all said tubular elements.

5. The reactor according to claim 4, wherein said nozzle (10) and said sleeve (20) are not permanently fixed to said first and second top plates (2) and (4) respectively.

* * * * *